United States Patent [19]

Whitehead

[11] 4,296,086

[45] Oct. 20, 1981

[54] MONITORING PROCESS AND APPARATUS

[75] Inventor: Paul Whitehead, Binfield Heath, England

[73] Assignee: Johnson, Matthey & Co., Limited, London, England

[21] Appl. No.: 101,857

[22] Filed: Dec. 10, 1979

[30] Foreign Application Priority Data

Dec. 15, 1978 [GB] United Kingdom ............ 48663/78

[51] Int. Cl.³ ................... G01N 21/78; C01B 21/06
[52] U.S. Cl. .................................. 423/392; 422/62;
422/83; 422/111; 423/403; 23/232 R
[58] Field of Search ..................... 923/392, 403, 404;
23/230 A, 232; 422/62, 83, 224, 111

[56] References Cited

U.S. PATENT DOCUMENTS

| 3,067,014 | 12/1962 | Morgan | 423/392 X |
| 3,081,153 | 3/1963 | Parsons | 423/392 |
| 3,718,429 | 2/1973 | Williamson | 422/83 |
| 3,808,327 | 4/1970 | Roberts | 423/402 |
| 3,835,322 | 9/1974 | Komatsu | 422/83 |
| 4,042,333 | 8/1977 | Dell et al. | 23/232 |

FOREIGN PATENT DOCUMENTS

| 769997 | 3/1957 | United Kingdom. |
| 1343858 | 1/1974 | United Kingdom. |
| 1343859 | 1/1974 | United Kingdom. |

*Primary Examiner*—G. O. Peters
*Attorney, Agent, or Firm*—Cushman, Darby & Cushman

[57] ABSTRACT

In a process and apparatus for maintaining the efficiency of ammonia oxidation in a nitric acid plant, the ammonia content of the reactant mixture and the nitrogen oxide content of the reaction product are determined by spectrometry, any nitric oxide in the sample of reaction product first being converted to nitrogen dioxide at elevated temperature and pressure. The apparatus comprises delay means for ensuring conversion of the sample of reaction product before analysis. Analysis may be by UV or IR spectrophotometry or by mass spectrography.

16 Claims, 1 Drawing Figure

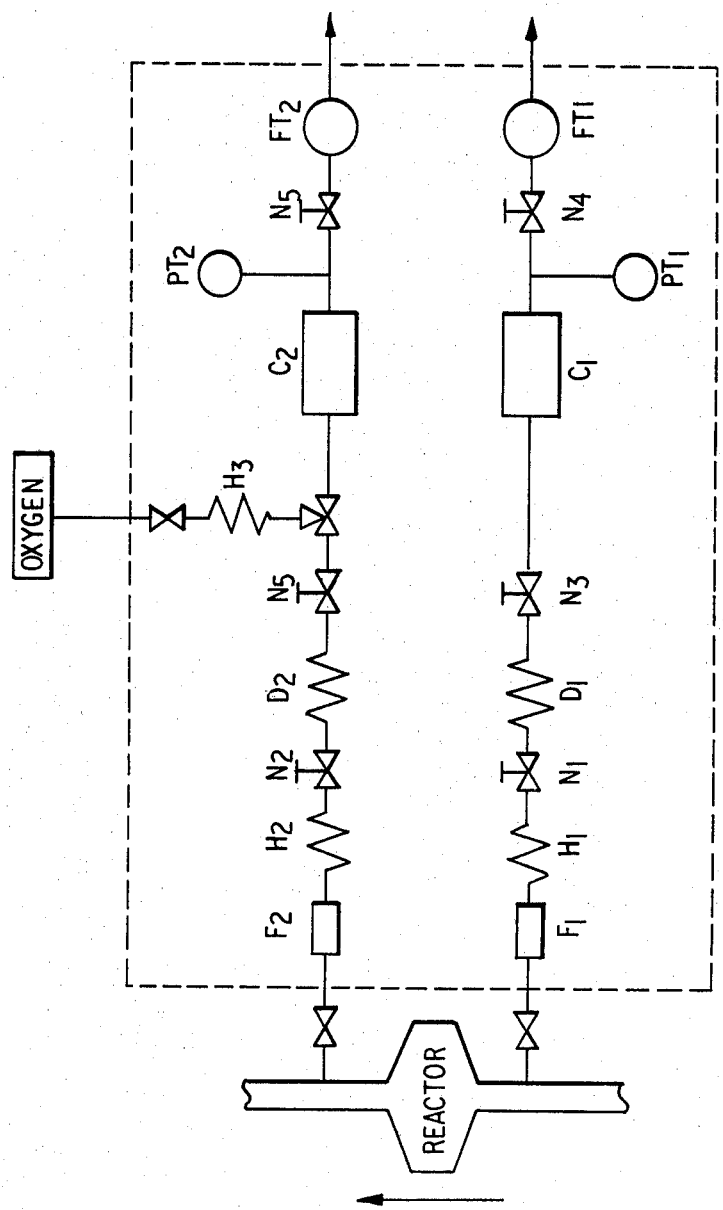

MONITORING PROCESS AND APPARATUS

This invention relates to a process of and apparatus for monitoring, in particular for monitoring the efficiency of conversion of ammonia to nitrogen oxides in the manufacture of nitric acid.

Nitric acid is made by the catalytic oxidation of ammonia in admixture with air to nitrogen oxides; it is a continuous process and there is a requirement for quick and reliable means of monitoring the efficiency of conversion so that appropriate and adjustments can be made to the operating conditions. Monitoring the efficiency of the conversion involves determining the proportion of ammonia in the reactant mixture and of nitrogen oxides in the reaction product. This is normally done by quantitative chemical analysis.

The present invention provides a monitoring process and equipment based on high precision spectrometry which has the advantage of speed and convenience and, if desired, of continuous and/or automatic operation.

According to the present invention a process of monitoring the ammonia oxidation conversion efficiency in a nitric acid plant comprises measuring the ammonia content in the reactant mixture and the nitrogen oxide content in the reaction product by spectrophotometric analysis, the nitrogen oxide content being determined after converting any nitric oxide in the reaction product to nitrogen dioxide at elevated pressure and temperature.

Preferably the conversion of nitric oxide to nitrogen dioxide is carried out at a pressure of at least 4 atmospheres and a temperature of from 125° to 225° C., preferably from 150° to 200° C. Because of this pressure requirement the process is most suitable for use in nitric acid plants operating at medium or high pressures.

Optionally the conversion can be carried out in the presence of a catalyst, such as silica gel.

When the proportion of ammonia in the reactant mixture is less than 10.3% v/v sufficient residual oxygen is present in the reaction product to convert any nitric oxide to nitrogen dioxide. At higher proportions of ammonia an oxidant should be added to the sample of reaction product to enable the conversion to be completed. A particularly suitable oxidant is oxygen.

Time must be allowed for conversion to take place between sampling the reaction product and measuring the nitrogen dioxide content and this may be done by passing the sample through a delay chamber, preferably a coil, in which it is maintained at the desired elevated temperature and pressure. This delay chamber may be packed with a catalyst for the conversion. The appropriate effective volume of the delay chamber depends on the flow rates but in general should be enough to provide a delay of at least five minutes, preferably at least ten minutes, the temperature and pressure in the chamber being adjusted to ensure adequate conversion during the delay time. A corresponding delay chamber may be provided in the ammonia sample line so that simultaneous readings can be taken on simultaneously drawn samples. This may be desirable when the process is operated with continuous flow of the samples through the apparatus.

Alternatively, the nitrogen oxide sample may be held in a holding chamber for completion of the conversion by an oxidant contained in or added to the chamber. In this latter case, the measurement is carried out batch wise on each converted sample.

Measurement of the ammonia and nitrogen dioxide contents may be carried out in a spectrophotometric cell using ultraviolet light, the degree of absorption of particular ranges of wavelengths of the light being determined. A particularly useful range of wavelengths is 200-220 nm, this being suitable for ammonia and for nitrogen dioxide at the concentration being measured. A small positive pressure, e.g. up to 2 atmospheres is preferably maintained in the cell.

Alternatively, the measurement may be carried out in a spectrophotometric cell using infra red, again measuring the degree of absorption of particular wavelengths. A suitable wavelength at which to measure ammonia content of the sample is 30 $\mu$m, and for nitrogen dioxide 3.43 $\mu$m.

As a further alternative, the measurement may be carried out in a mass spectrograph. This involves measurement of nitrogen dioxide at mass 46, ammonia at mass 17 and water at mass 18. The latter is required to correct the measurement at mass 17 for hydroxyl content. Measurement of argon at mass 40 may also be used for standardisation of the instrument.

The present invention also provides apparatus suitable for such a process of monitoring the efficiency of ammonia oxidation conversion in a nitric acid plant operating at medium or high pressure comprising:
  means for sampling the reactant mixture and the reaction product and passing the sample to spectrometric measuring instruments;
  means for providing a time of passage of the nitrogen oxide sample between the sampling point and the instrument sufficient to permit conversion of any nitric oxide in the sample to nitrogen dioxide;
  when necessary, means for treating the reaction product sample with an oxidant to complete the conversion of nitric oxide to nitrogen dioxide;
  means for maintaining the samples at elevated temperature and pressure during the passage between sampling point and measuring instrument;

When the measuring intrument is a UV or IR spectrophotometer, the cell must be temperature controlled. Additionally, when the sampling and measurement is continuous the apparatus should also comprise means to control the flow rate of the samples and the pressure in the spectrophotometric cells.

Where the measurement is carried out by UV spectrophotometry the apparatus also comprises means for passing a beam of ultra-violet light of a predetermined range of wavelengths through the cells and for measuring the degree of absorption of the light beam. A corresponding means is provided where the measurement is by IR spectrophotometry. In the case of mass spectrography a bleed line for conveying samples to the mass spectrograph may be provided.

Preferably the means for extending the time of passage of the reaction product sample is a delay coil, which optionally may contain a catalyst for the conversion. Alternatively, it may be a holding chamber which may contain a solid oxidant such as manganese dioxide or may be provided with means for adding oxygen to a sample held in the chamber. As a further alternative, the holding chamber may be additional to the delay chamber or, when oxygen is to be used, the spectrophotometric cell itself may be used as a holding chamber.

In the case of UV measurement of the samples, a suitable source of the ultra-violet light is a deuterium lamp. The degree of absorption of the light beams may be measured by a suitable photo-multiplier. Advantageously, an alternative channel for a reference beam which by-passes the cells is provided in spectrophotometric systems for use in calibration and monitoring drift.

Conveniently, the apparatus, including the cells when spectrophotometric measurement is used, are contained in a temperature controlled chamber to facilitate stabilisation of the samples and maintain them in that condition during measurement. The chamber is preferably maintained at a temperature of from 125° to 225° C., more preferably from 150° to 200° C.

The invention is illustrated by the following description and with reference to the accompanying flow sheet.

In a nitric acid plant sampling lines are provided before and after the catalytic oxidation reactor. The two sampling lines are each provided with filters F, preheat coils H, delay coils D, spectrophotometric cells C, pressure monitors PT, flow monitors FT and needle valves N. All these are enclosed in a temperature-controlled oven. In addition the nitrogen oxide sampling line is provided with an oxygen line fitted with a preheat coil H.

The spectrophotometric cells are quartz cells which lie in the light path produced by an optical system (not shown) comprising a deuterium lamp source, the beam from which is collimated and passed through a filter and a beam splitter. After passing through the cells the beam passes through a further splitter and a filter to a photomultiplier. A reference channel is provided via the beam splitters and is used to monitor drift.

In operation, samples are drawn from the nitric acid plant, the ammonia-containing sample being drawn before the catalytic oxidation reactor and the nitrogen oxide-containing sample after the reactor. The sampling lines pass into the oven which is maintained at 175° C. The samples are filtered through filters $F_1$ and $F_2$ and the temperature and pressure adjusted by the preheating coils $H_1$ and $H_2$ and needle valves $N_1$ and $N_2$ respectively. The samples are maintained at a temperature of 175° C. and a pressure of 4 to 8 atmospheres in the delay coils $D_1$ and $D_2$ and the pressure is reduced to between one and two atmospheres in the photometric cell by needle valves $N_3$, $N_4$, $N_5$ and $N_6$. This pressure is measured by monitors $PT_1$ and $PT_2$. After passing through the flow monitors $FT_1$ and $FT_2$ the samples are vented. In this case the flow of the samples may be continuous.

When required, oxygen preheated in coil $H_3$ may be added to the sample in cell $C_2$ which is retained there until conversion of the nitric oxide content is complete; the nitrogen dioxide content is then measured. In this case the measurement of the reaction product sample is batchwise; if desired, the measurement of the reactant mixture sample may be correspondingly batchwise on a sample taken substantially simultaneously.

The apparatus may be calibrated by feeding into the appropriate cell a mixture containing a known proportion of ammonia or nitrogen dioxide and measuring and degree of absorption of the ultra-violet light. Suitably, the apparatus may be provided with means for flushing out with an inert gas such as nitrogen.

Alternatively, the calibration may be carried out be chemical analysis of simultaneously drawn samples. In a check of results obtained using the calibrated apparatus against results obtained by titrimetry:

two reaction product samples showed 15.68 and 15.98 nitrogen dioxide as % w/w in nitrogen when measured by the former method and 15.6 and 15.9% when measured by the latter method, and two reactant mixture samples showed 6.15 and 6.16 w/w % ammonia when measured by the former method and 6.13 and 6.18% when measured by the latter method.

As an alternative to controlling pressure by needle valves as described above, the apparatus may be provided with automatic pressure controllers in the sample flow lines.

In another alternative construction the delay coil $D_2$ may be replaced by a delay chamber into which oxygen from the heating coil $H_3$ may be fed when desired. In this latter case, the oxygenated sample is held in the chamber until conversion and stabilisation is completed before passing it batchwise to the measuring instrument. Where additional oxygen is not required, the apparatus may be used in a continuous sampling and measuring mode provided that the capacity of the chamber, in relation to temperature, pressure and flow-rate of the sample of reaction product, is adequate for conversion of nitric oxide to nitrogen dioxide. In either case, the delay coil $D_1$ may also be omitted, allowance then being made for the time lag in analysis of a sample of reaction product as compared with analysis of a simultaneously drawn sample of reactant mixture.

The operation of the process and apparatus of this invention may conveniently be controlled by a suitable programmed microprocessor.

I claim:

1. A process of monitoring the ammonia oxidation conversion efficiency in a nitric acid plant which comprises taking samples of the reactant mixture and of the reaction product, and measuring both the ammonia content in the sample of reactant mixture and the nitrogen oxide content in the sample of reaction product by ultraviolet spectrophotometry using ultraviolet light of wavelength 200–220 nm, the nitrogen oxide content in the sample of reaction product being measured after converting any nitric oxide in said sample to nitrogen dioxide at elevated temperature and pressure.

2. A process as claimed in claim 1 in which the conversion is carried out at an elevated temperature of from 125°–225° C.

3. A process as claimed in claim 1 in which the conversion is carried out at a pressure of at least 4 atmospheres.

4. A process as claimed in claim 1 in which the sampling and measurement are carried out continuously, the conversion taking place in a delay coil.

5. A process as claimed in claim 1 in which in the conversion to nitrogen dioxide, the sample is treated with an oxidant.

6. A process as claimed in claim 5 in which the oxidant is oxygen.

7. A process as claimed in claim 6 in which the sample and the oxygen are mixed and held in a holding chamber until the products of the resulting conversion have been stabilised at a temperature suitable for analysis.

8. A process as claimed in claim 1 in which conversion is carried out in the presence of a catalyst.

9. A process as claimed in claim 1 in which the analysis is carried out at the same temperature as the conversion.

10. Apparatus suitable for the process of claim 1 comprising:

(1) means for sampling the reactant mixture and the reaction product and passing the samples to spectrometric measuring instruments,
(2) means for providing a time of passage of the nitrogen oxide sample between the sampling point and the instrument sufficient to permit conversion of any nitric oxide in the sample to nitrogen dioxide,
(3) means for maintaining the samples at elevated temperature and pressure during the passage between sampling point and measuring means, and
(4) measuring means for ultraviolet spectrophotometric analysis of both said samples by the use of ultraviolet light of wavelength 200–220 nm.

11. Apparatus as claimed in claim 10 having a delay means containing a catalyst for conversion of the nitrogen oxide sample.

12. Apparatus as claimed in claim 10 having means for contacting the sample of reaction product with an oxidant for conversion of nitric oxide to nitrogen dioxide.

13. Apparatus as claimed in claim 12 having a chamber in which the sample of reaction product may be mixed with oxygen as the oxidant.

14. Apparatus as claimed in claim 10 having a delay chamber for holding the sample of reactant mixture for a time corresponding to the delay provided by means (2) for conversion of the sample of reaction product before said samples are passed to said measuring means (4).

15. Apparatus as claimed in claim 10 in which the sample of reaction product may be mixed with oxygen as oxidant in the cell of the spectrophotometer.

16. Apparatus as claimed in claim 10 in which the means for passing the samples to the measuring instruments, the means to permit conversion of the reaction product and the cells of spectrophotometric instruments where used are enclosed in a temperature controlled chamber which can be maintained at a temperature of from 125° to 250° C.

* * * * *